(12) United States Patent
Kim

(10) Patent No.: US 8,778,444 B2
(45) Date of Patent: Jul. 15, 2014

(54) METHOD FOR MANUFACTURING WIRE FOR DENTAL CORRECTION

(75) Inventor: In Jae Kim, Gyeonggi-do (KR)

(73) Assignee: Seongsuk Choe, Gyeonggi-do (KR)

(*) Notice: Subject to any disclaimer, the term of this patent is extended or adjusted under 35 U.S.C. 154(b) by 375 days.

(21) Appl. No.: 13/130,122

(22) PCT Filed: Nov. 11, 2009

(86) PCT No.: PCT/KR2009/006614
§ 371 (c)(1),
(2), (4) Date: May 19, 2011

(87) PCT Pub. No.: WO2010/058925
PCT Pub. Date: May 27, 2010

(65) Prior Publication Data
US 2011/0220612 A1 Sep. 15, 2011

(30) Foreign Application Priority Data
Nov. 21, 2008 (KR) .................. 10-2008-0116419

(51) Int. Cl.
*A61C 3/00* (2006.01)
*B05D 5/00* (2006.01)

(52) U.S. Cl.
USPC .......... 427/2.29; 427/256; 427/261; 427/264; 433/20

(58) Field of Classification Search
USPC ........................................ 427/2.29; 433/20
See application file for complete search history.

(56) References Cited

U.S. PATENT DOCUMENTS

| 4,946,387 A | * | 8/1990 | Adell | ............................. | 433/20 |
| 5,063,082 A | | 11/1991 | Adell | | |
| 6,736,637 B2 | * | 5/2004 | Bond | ............................. | 433/20 |

FOREIGN PATENT DOCUMENTS

| KR | 20070015629 A | | 2/2007 |
| KR | 10-20070107633 | | 11/2007 |
| KR | 2007107633 A | * | 11/2007 |
| KR | 100795106 | | 1/2008 |
| KR | 100853873 | | 8/2008 |
| WO | WO 9729712 A1 | | 8/1997 |
| WO | WO 2008147066 A2 | * | 12/2008 |

OTHER PUBLICATIONS

Search Report for PCT/KR2009/006614, dated Jul. 20, 2010, 2 pages.
Abstract of Chinese Patent—CN2462878, Dec. 5, 2001, 1 page.

* cited by examiner

*Primary Examiner* — Cachet Sellman
(74) *Attorney, Agent, or Firm* — Dority & Manning, P.A.

(57) ABSTRACT

A method of manufacturing a wire for straightening irregular teeth, which is not harmful to a human body and preserves the color of the teeth, is provided. The method of manufacturing a wire for straightening irregular teeth includes manufacturing a metal wire with metal alloy; physically or chemically etching a surface of the metal wire and then performing heat treatment; coating the surface of the metal wire with a metal material, Teflon, epoxy or urethane to show white or ivory and then performing heat treatment; forming a transparent parylene film on the metal material, Teflon, epoxy or urethane and then performing heat treatment; and removing one side of the foregoing coating layer from the surface of the metal wire, and then applying surface treatment to the one side with the coating layer removed.

16 Claims, 12 Drawing Sheets

METHOD FOR MANUFACTURING WIRE FOR DENTAL CORRECTION

CROSS REFERENCE TO RELATED APPLICATION

This application is the national stage entry of International Patent Application No. PCT/KR2009/006614 having a filing date of Nov. 11, 2009, which claims priority to and the benefit of Korean Patent Application No. 10-2008-0116419 filed in the Korean Intellectual Property Office on Nov. 21, 2008, the entire contents of which are incorporated herein by reference.

TECHNICAL FIELD

The present invention relates to a method of manufacturing a wire for straightening irregular teeth, and more particularly, to a method of manufacturing a wire for straightening irregular teeth, which is not harmful to a human body and preserves the color of the teeth.

BACKGROUND ART

For example, periodontal tissue is sequentially damaged from the edge of gums and alveolar bone is gradually lost as periodontitis proceeds, and thus so-called pyorrhea alveolaris that the tooth around the periodontitis is loose appears. As treatment for the pyorrhea alveolaris, a very loose tooth being hopeless of preservation is extracted, but a tooth being loose but hopeful of preservation is fixed together with an inconsiderably loose tooth adjacent thereto.

When a plurality of teeth adjacent to each other is fastened, a metal wire is generally used. In this method, the plurality of teeth to be fastened is wound with the metal wire while using the elasticity of the metal wire, and a load caused by the tensile and bend characteristics of the metal wire is applied to these teeth, so that the teeth can be fixed by this load.

However, the foregoing method has problems that man hours are needed in sequentially wounding and attaching the metal wire around the teeth, a patient always feels pain and his/her displeasure with the added load, and the metal wire stands out in front and looks ugly when opening his/her mouth.

Accordingly, there have recently been proposed methods of fixing a set of teeth using shape memory alloy. In these methods, a straightening member of a shape memory alloy wire previously undergoes heat treatment so that a shape in a parent phase can have a desired shape, i.e., a shape corresponding to an anatomically even set of teeth, and this straightening member is installed in accordance with the patient's set of teeth at low temperature and straightens the irregular teeth by returning to its original shape when warmed.

FIG. 1 shows a schematic view and a cross-section view of a conventional wire for straightening irregular teeth.

As shown in (a) of FIG. 1, a wire 10 for straightening irregular teeth looks similar to a general wire on the exterior. However, the wire 10 for straightening irregular teeth is internally different from the general wire, and therefore the shape and the manufacturing process thereof will be described in short with reference to (b) of FIG. 1.

(b) of FIG. 1 shows a cross-section taken from "A" in the wire 10 for straightening irregular teeth shown in (a) of FIG. 1.

Referring to (b) of FIG. 1, the conventional wire 10 for straightening irregular teeth includes a metal wire 11, and a Teflon coating film 13 formed on the surface of the metal wire 11. The metal wire 11 may be a general metal wire or a wire made of shape memory alloy. Further, the Teflon coating film 13 is coated on the metal wire 11 by various coating methods. The color of the Teflon coating film 13 is similar to the color of teeth.

As above, the conventional wire for straightening the irregular teeth is formed by coating the surface of the metal wire with the Teflon coating film in order to color the teeth. However, Teflon is being debated because of its toxic properties. A need for providing a wire for straightening irregular teeth, which is harmless to a human body, is urgent.

DISCLOSURE

Technical Problem

Accordingly, the present invention is conceived to solve the forgoing problems, and an aspect of the present invention is to provide a method of manufacturing a wire for straightening irregular teeth, which is not harmful to a human body and preserves the color of the teeth.

Technical Solution

In accordance with an aspect of the present invention, there is provided a method of manufacturing a wire for straightening irregular teeth, the method including manufacturing a metal wire with metal alloy; physically or chemically etching a surface of the metal wire and then performing heat treatment; coating the surface of the metal wire with a metal material, Teflon, epoxy or urethane to show white or ivory and then performing heat treatment; forming a transparent parylene film on the metal material, Teflon, epoxy or urethane and then performing heat treatment; and removing one side of the foregoing coating layer from the surface of the metal wire, and then applying surface treatment to the one side with the coating layer removed.

In accordance with another aspect of the present invention, there is provided a method of manufacturing a wire for straightening irregular teeth, the method including manufacturing a metal wire with metal alloy; physically or chemically etching a surface of the metal wire and then performing heat treatment; coating the surface of the metal wire with a metal material, Teflon, epoxy or urethane to show white or ivory and then performing heat treatment; coating a transparent metal oxide film on the metal material, Teflon, epoxy or urethane coated on the surface of the metal wire; forming a transparent parylene film on the transparent metal oxide film and then performing heat treatment; and removing one side of the foregoing coating layer from the surface of the metal wire, and then applying heat treatment to the one side with the coating layer removed.

In accordance with still another aspect of the present invention, there is provided a method of manufacturing a wire for straightening irregular teeth, the method including manufacturing a metal wire with metal alloy; masking a posterior part and one side of an anterior part of the metal wire with a mask capable of surrounding the posterior part and the one side of the anterior part of the metal wire; physically or chemically etching a surface of the metal wire and then performing heat treatment; coating the surface of the metal wire with a metal material, Teflon, epoxy or urethane to show white or ivory and then performing heat treatment; and forming a transparent parylene film on the metal material, Teflon, epoxy or urethane and then performing heat treatment.

In accordance with still another aspect of the present invention, there is provided a method of manufacturing a wire for straightening irregular teeth, the method including manufacturing a metal wire with metal alloy; masking a posterior part and one side of an anterior part of the metal wire with a mask capable of surrounding the posterior part and the one side of the anterior part of the metal wire; physically or chemically etching a surface of the metal wire and then performing heat treatment; coating the surface of the metal wire with a metal material, Teflon, epoxy or urethane to show white or ivory and then performing heat treatment; coating a transparent metal oxide film on the metal material, Teflon, epoxy or urethane coated on the surface of the metal wire; and forming a transparent parylene film on the transparent metal oxide film and then performing heat treatment.

In accordance with still another aspect of the present invention, there is provided a method of manufacturing a wire for straightening irregular teeth, the method including manufacturing a metal wire with metal alloy; forming a masking parylene film on a surface of the metal wire and then removing the masking parylene film from one side of the metal wire or one side of an anterior part; physically or chemically etching a surface of the one side of the metal wire with the masking paraylene film removed and then performing heat treatment; coating a metal material, Teflon, epoxy or urethane of the surface of the one side of the metal wire, from which the masking parylene film is removed, to show white or ivory and then performing heat treatment; forming a transparent parylene film on the metal material, Teflon, epoxy or urethane and then performing heat treatment; and removing the masking paryelene film remaining on the metal wire and the coating layer on the masking parylene film.

The metal wire may include one of stainless steel, NiTi, nickel (Ni) alloy, titanium (Ti) alloy, copper (Cu) alloy, and aluminum (Al) alloy.

The metal wire may be wet cleaned using alkali, organic solvent, or ultra-pure water before physically or chemically etching the surface of the metal wire.

The surface of the metal wire may be etched with an etching solution produced by mixing one or mixture of $CuCl_2$, $FeCl_3$, $HCl$, $H_2SO_4$, $HNO_3$, $H_3PO_4$, $HF$ and $H_2O_2$ with $H_2O$ or an organic solvent.

The metal wire may be electro- or electroless-etched to undergo the surface treatment.

The metal wire may undergo the surface treatment to have a curve with a width and depth of 0.1 μm to 50 μm.

The surface-treated metal wire may be wet-cleaned with one of alkali, organic solvent and water.

The heat treatment performed after physically or chemically etching the surface of the metal wire may be carried out at atmospheric pressure or in a vacuum chamber, and proceeded for 1 minute to 48 hours at temperature of 50 to 300° C.

The metal material coated on the surface of the metal wire may be based on wet electroplating or dry plating.

The metal material coated on the surface of the metal wire may include one or mixture among silver (Ag), zinc (Zn), tin (Sn), indium (In), platinum (Pt), tungsten (W), nickel (Ni), chrome (Cr), aluminum (Al), palladium (Pd), and gold (Au).

The metal material may be coated having a thickness of 0.1 to 20 μm on the surface of the metal wire.

The metal material coated on the surface of the metal wire may be formed by one of plasma sputtering, thermal vacuum evaporation, e-beam evaporation, ion plating, vacuum spraying, and wet electroplating.

The surface of the metal wire may be coated with the white or ivory metal material, Teflon, epoxy or urethane, and then cleaned with ultrasonic waves using alkali, organic solvent, or ultra-pure water.

The heat treatment performed after coating the metal material, Teflon, epoxy or urethane may be carried out at atmospheric pressure or in a vacuum chamber, and proceeded for 1 minute to 48 hours at temperature of 50 to 600° C.

The surface of the white or ivory metal material, Teflon, epoxy or urethane may be chemically etched and undergoes heat treatment.

The surface of the metal wire may be etched with an etching solution produced by mixing one or mixture of $HCl$, $H_2SO_4$, $HNO_3$ and $H_2O_2$ with $H_2O$.

The surface of the metal material may be etched for 1 second to 5 minutes at temperature of 10 to 100° C.

The heat treatment performed after chemically etching the surface of the metal material, Teflon, epoxy or urethane may be carried out at atmospheric pressure or in a vacuum chamber, and proceeded for 1 minute to 48 hours at temperature of 50 to 600° C.

The transparent metal oxide film may be formed by coating a raw material of nano-sized particles in a sol state through a vacuum spraying method.

The transparent metal oxide film may be formed by one of sputtering, thermal vacuum evaporation, e-beam evaporation, and ion plating.

The transparent metal oxide film may include one or mixture of ITO, ZnO, $TiO_2$, $Al_2O_3$, $Ta_2O_5$, $ZrO_2$, $SiO_2$, $GeO_2$, $Y_2O_3$, $La_2O_3$, $HfO_2$, CaO, $In_2O_3$, $SnO_2$, MgO, $WO_2$, and $WO_3$.

The transparent metal oxide film may be coated to have a thickness of 1 nm to 1 μm.

The transparent metal oxide film may be coated in a vacuum chamber at temperature of 15° C. to 300° C.

The transparent parylene film may include at least one of C(Di-chloro-para-xylylene)-type, N(Di-para-xylylene)-type, D(Tetra-chloro-para-xylylene)-type, F(Octafluoro-[2,2]para-xylylene)-type, HT-type, A-type, and AM-type dimers.

The thickness of the transparent parylene film may range from 1 μm to 50 μm.

The heat treatment performed after forming the transparent parylene film may be carried out at atmospheric pressure or in a vacuum chamber, and proceeded for 1 minute to 48 hours at temperature of 50° C. to 250° C.

Advantageous Effects

In accordance with a method of a wire for straightening irregular teeth with the foregoing configuration and operation according to exemplary embodiments of the present invention, the wire for straightening irregular teeth is coated with the transparent metal material and then coated again with the transparent parylene film, so that the transparent metal material showing tooth color can be prevented from discoloration and coherence between the wire and the teeth can decrease dislike.

Also, the parylene film is coated on the outmost surface, and it is thus harmless to a human body and has a soft texture, thereby having an effect on giving more improved wearability to the teeth.

BEST MODE

Hereinafter, operations and exemplary embodiments of a method of manufacturing a wire for straightening irregular teeth with the foregoing configuration will be described according to an exemplary embodiment of the present invention.

Figure 1A:
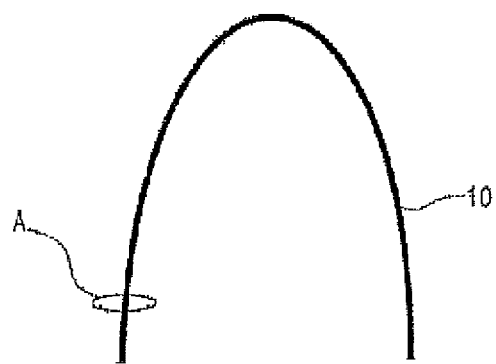
FIG. 1 shows a schematic view and a cross-section view of a conventional wire for straightening irregular teeth.
Figure 1B:
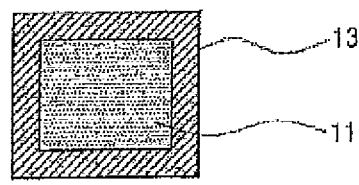
Figure 2A:
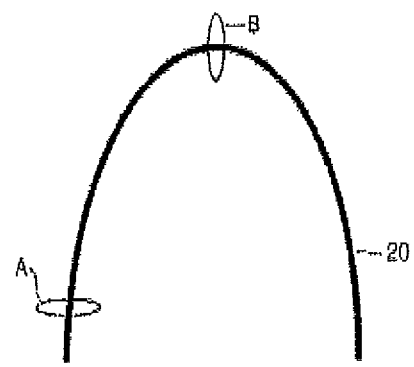
FIG. 2 shows a schematic view and a cross-section view of a wire for straightening irregular teeth according to an exemplary embodiment of the present invention.
Figure 2B:
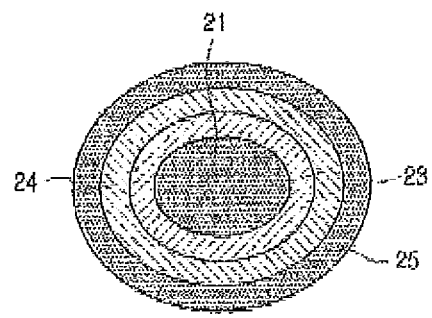
Figure 2C:
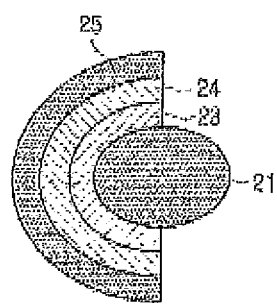

FIG. 2 shows a schematic view and a cross-section view of a wire for straightening irregular teeth according to an exemplary embodiment of the present invention.

As shown in (a) of FIG. 2, a wire 20 for straightening irregular teeth looks similar to a general wire on the exterior. However, the wire 20 for straightening irregular teeth is internally different from the general wire, and therefore the shape and the manufacturing process thereof will be described with reference to (b) and (c) of FIG. 2.

(b) of FIG. 2 shows a cross-section taken from "A" in the wire 20 for straightening irregular teeth shown in (a) of FIG. 2, and (c) of FIG. 2 shows a cross-section taken from "B" in the wire 20 for straightening irregular teeth shown in (a) of FIG. 2.

Referring to (b) of FIG. 2, the wire 20 for straightening irregular teeth according to an exemplary embodiment of the present invention includes a long metal wire 21, and a white metal material 23 coated on to a surface of the metal wire 21, a transparent metal oxide film 24 coated on to a surface of the metal material 23, and a transparent parylene film 25 formed on the transparent metal oxide film 24. The transparent metal oxide film 24 may exist or may not exist between the white metal material 23 and the transparent parylene film 25.

Meanwhile, referring to (c) of FIG. 2, one side of an anterior part of the metal wire 21 is not coated with the white metal material 23, the transparent metal oxide film 24, the transparent parylene film, etc.

Figure 3:
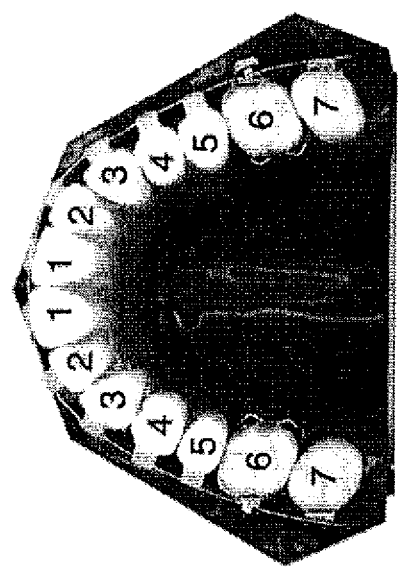
FIG. 3 shows a schematic view of explaining anterior and posterior parts of a tooth according to an exemplary embodiment of the present invention.

Here, as shown in FIG. 3, the anterior part includes the left $3^{rd}$ tooth to the right $3^{rd}$ tooth, or the left $5^{th}$ tooth to the right $5^{th}$ tooth, and the posterior part includes the others. Meanwhile, (b) of FIG. 2 shows that the metal wire corresponding to the posterior part is coated with all of the white metal material 23, the transparent metal oxide film 24, and the transparent parylene film, but not limited thereto. Alternatively, as shown in (c) of FIG. 2, one side of the metal wire may be not coated with the white metal material 23, the transparent metal oxide film 24, the transparent parylene film, etc.

The metal wire 21 is made of metal alloy containing general metal material and shape memory alloy. The metal alloy for the metal wire 21 may contain one of stainless steel, NiTi, nickel (Ni) alloy, titanium (Ti) alloy, copper (Cu) alloy, and aluminum (Al) alloy.

If general metal is transformed exceeding its elastic limit, the metal does not return to its original shape even though it is heated or cooled. However, certain alloy formed to have a proper shape at high temperature returns to the shape when heated again even though it is transformed at room temperature.

This effect is called a shape memory effect, which is because the alloy remembers the given shape as arrangement of atoms. This effect is shown in the alloy which is not diffused but transformed. The parent phase atomic arrangement at high temperature is remembered even when it is transformed at low temperature, so that the original arrangement of atoms can return at high temperature.

This effect generates a great force while returning the shape. Since the force is generated, the shape memory allow can be used not only as a sensor but also for tightening a machinery part. Accordingly, the metal wire made of the shape memory alloy can be used in straightening the irregular teeth.

The metal material 23 coated on the surface of the metal wire 21 containing the shape memory alloy and the general metal alloy makes the metal wire 21 show white similarly to the color of the teeth.

The metal material 23 coated on the surface of the metal wire 21 is based on wet electroplating or dry plating.

The white metal material 23 coated on the surface of the metal wire 21 may be one or mixture of at least two among silver (Ag), zinc (Zn), tin (Sn), indium (In), platinum (Pt), tungsten (W), nickel (Ni), chrome (Cr), aluminum (Al), palladium (Pd), and gold (Au).

The transparent metal oxide film 24 may be coated on the surface of the white metal material 23, in which the transparent metal oxide film 24 is formed by vacuum deposition of one or mixture of ITO, ZnO, $TiO_2$, $Al_2O_3$, $Ta_2O_5$, $ZrO_2$, $SiO_2$, $GeO_2$, $Y_2O_3$, $La_2O_3$, $HfO_2$, CaO, $In_2O_3$, $SnO_2$, MgO, $WO_2$, and $WO_3$.

The transparent metal oxide film 24 may have a thickness of 1 nm to 1 μm. Further, the transparent metal oxide film 24 having such a thickness may be formed by one of plasma sputtering, e-beam evaporation, thermal evaporation, and ion plating. Also, a raw material of nano-sized particles in a sol state may be coated by a vacuum spraying method to form the transparent metal oxide film 24.

The transparent parylene film 25 of a high molecular compound is coated on the white metal material 23 or the transparent metal oxide film 24. The transparent parylene film 25 coated on the transparent metal oxide film 24 may have a thickness of 1 μm~50 μm.

The parylene is a material proven to be harmless to a human body, can be uniformly coated on the surface of the transparent metal oxide film 24, and has good surface illuminative properties and a soft texture. Thus, if a patient wears the wire for straightening irregular teeth coated with the parylene, s/he can feel a good texture.

With this configuration, a method of manufacturing the wire for straightening irregular teeth according to an exemplary embodiment of the present invention will be described.

A method of manufacturing the wire for straightening irregular teeth according to a first exemplary embodiment of the present invention includes manufacturing a metal wire with metal alloy; applying heat treatment to the metal wire after physically or chemically etching the surface of the metal wire; applying heat treatment to the metal wire after coating the metal wire with a metal material, Teflon, epoxy or urethane so that the surface of the metal wire can color white or ivory; applying heat treatment to the metal wire after forming the transparent parylene film on the metal material, the Teflon, the epoxy or the urethane; and removing one side of the foregoing coating layer on the surface of the metal wire and applying surface treatment to the one side.

A method of manufacturing the wire for straightening irregular teeth according to a second exemplary embodiment of the present invention may include coating the transparent metal oxide film on the metal material, Teflon, epoxy or urethane of the metal wire before forming the transparent parylene film on the white or ivory metal material, Teflon, epoxy or urethane. That is, the heat treatment is performed after the metal material, Teflon, epoxy or urethane is coated on the surface of the metal wire so that the metal wire can color white or ivory, and then the transparent metal oxide is coated on the metal material, Teflon, epoxy or urethane. Then, the transparent parylene film is formed on the transparent metal oxide, and then the heat treatment is performed.

A method of manufacturing the wire for straightening irregular teeth according to a third exemplary embodiment of the present invention may include a masking process in addition to the manufacturing method according to the first exemplary embodiment.

That is, the method of manufacturing the wire for straightening irregular teeth according to the third exemplary embodiment of the present invention further includes masking one side of the anterior part and the whole posterior part of the metal wire with a mask capable of covering one side of the anterior part and the posterior part of the metal wire, before physically or chemically etching the surface of the metal wire.

Here, the posterior part of the metal wire indicates a part of the wire for straightening the irregular teeth, which can straighten a molar tooth (see FIG. 3). Likewise, the anterior part of the metal wire indicates a part for straightening a front tooth and a canine tooth.

The reason why the posterior part of the metal wire for straightening the molar tooth is masked as above is because only metal wire coated with no parylene film is needed for straightening the molar tooth. More force is needed to straighten the molar tooth than that for the canine tooth or the front tooth. Further, the wire for straightening the irregular teeth has to have a good sliding effect during a straightening procedure.

As above, in order to apply more force to the molar tooth and improve the sliding effect, a part of the wire for straightening the irregular teeth, i.e., the posterior part for straightening the molar tooth is not coated with the parylene film but has only the metal wire. Thus, a process of masking the posterior part of the metal wire with the mask is needed while manufacturing the wire for straightening the irregular teeth.

Meanwhile, the reason why the one side of the anterior part is masked is because an externally exposed part is needed to be coated with white or ivory color for a beautiful outer appearance and one side of the metal wire for contacting and straightening the teeth is needed not to be coated for having the foregoing effect (i.e., sliding effect).

Figure 4:
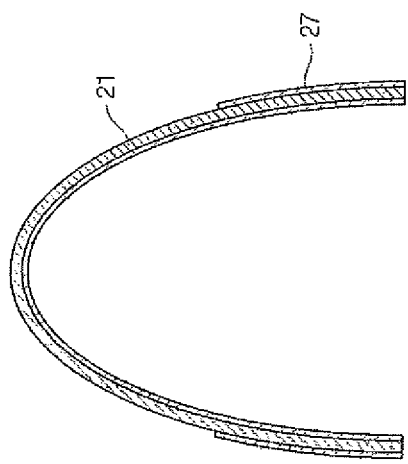
FIG. 4 shows an example where one side of an anterior part and a posterior part of a metal wire are masked according to another exemplary embodiment of the present invention.

FIG. 4 shows that the whole posterior part and the one side of the anterior part of the metal wire 21 are masked with the mask. As a method of masking the posterior part and one side of the anterior part of the metal wire 21 with the mask, a tube 27 made of an elastic material or a box in which the posterior part or the one side of the anterior part can be inserted may be mounted to the posterior part and one side of the anterior part of the metal wire 21. At this time, the elastic tube 27 or box to be used as the mask may be made of polymer or a metal material. For example, the mask may be made of polymer such as silicon or the like, or rubber such as urethane or the like.

As another method of masking the whole posterior part and the one side of the posterior part of the metal wire 21, there may be used a masking jig for preventing the whole posterior part or the one side of the posterior part from being exposed to the outside. Thus, the whole posterior part and the one side of the posterior part can be prevented from being coated with the parylene. The masking jig is made of polymer, metal or rubber, and masks and fixes the posterior part and the one side of the anterior part. Then, the whole posterior part and the one side of the posterior part are coated with no parylyene even through the parylene coating is performed.

In the foregoing exemplary embodiment, the whole posterior part and the one side of the posterior part are masked, but not limited thereto. Alternatively, a part to be masked may be changed. For example, only one side of the whole metal wire may be masked.

In the meantime, a method of manufacturing the wire for straightening the irregular tooth according to a fourth exemplary embodiment of the present invention includes coating the transparent metal oxide film in addition to the manufacturing method according to the third exemplary embodiment.

That is, the method of manufacturing the wire for straightening the irregular tooth according to the fourth exemplary embodiment further performs not only masking the whole posterior part and one side of the anterior part of the metal wire before physically or chemically etching the surface of the metal wire, but also coating the transparent metal oxide flm on the white or ivory metal material, Teflon, epoxy or urethane before forming the transparent parylene film on the white or ivory metal material, Teflon, epoxy or urethane. Thus, the transparent metal oxide film is formed between the white or ivory metal material, Teflon, epoxy or urethane and the transparent parylene film.

In the meantime, a method of manufacturing the wire for straightening the irregular tooth according to a fifth exemplary embodiment of the present invention is configured to coat the posterior part and the one side of the anterior part of the metal wire with no parylene film like those of the third and fourth exemplary embodiments. However, the parylene film is used as a masking means instead of the tube or the jig.

Figure 5:
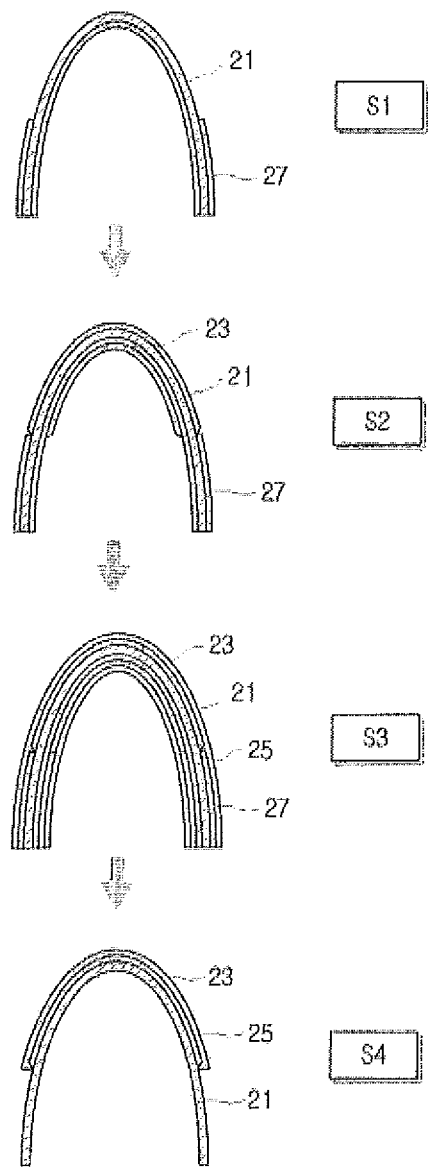
FIG. 5 shows a manufacturing process of a wire for straightening irregular teeth, of which one sides of anterior and posterior parts of a metal wire are not coated with a parylene film, according to another exemplary embodiment of the present invention.
Figure 6A:
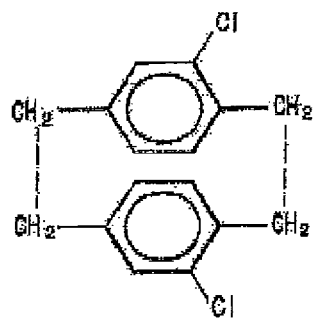
FIG. 6 shows structural formulas of dimers according to an exemplary embodiment of the present invention.
Figure 6B:
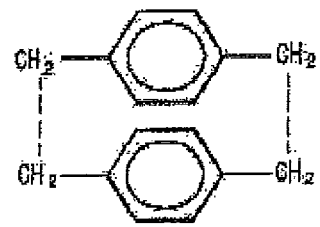
Figure 6C:
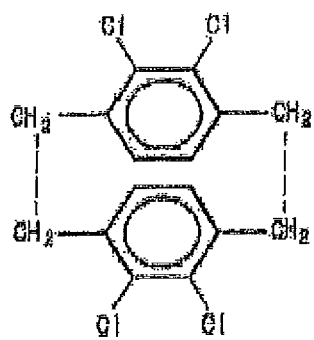
Figure 6D:
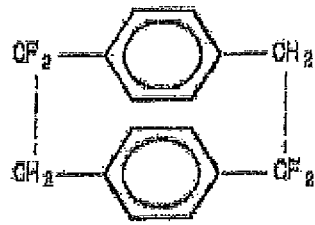
Figure 6E:
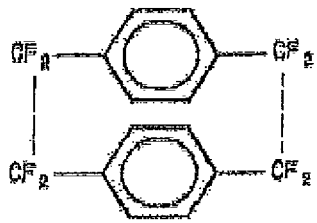
Figure 6F:
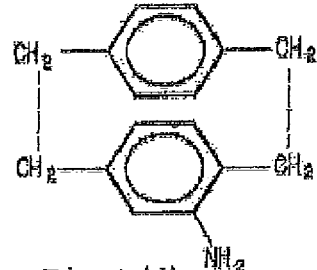
Figure 6G:
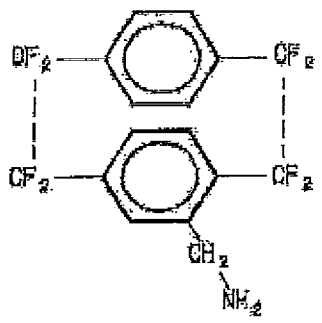

FIG. 5 shows a manufacturing method of the wire for straightening the irregular teeth according to the fifth exemplary embodiment of the present invention.

As shown in FIG. 5, the manufacturing method of the wire for straightening the irregular teeth according to the fifth exemplary embodiment of the present invention is performed as follows.

First, the metal wire 21 is manufactured with metal alloy, and a masking parylene film 27 is formed on the whole surface of the metal wire 21. Then, the masking parylene film 27 is removed from one side of the metal wire 21 or one side of the anterior part (S1). In other words, the masking parylene film is removed from one side of the whole metal wire, or from only one side of the anterior part.

Then, the surface of the one side of the metal wire 21, from which the masking parylene film is removed, is physically or chemically etched, and then undergoes heat treatment. This process is performed so that the metal material, Teflon, epoxy or urethane can be smoothly coated in the next process. That is, the heat treatment is performed after the etching process so that the metal material or the like can be easily coated on the metal wire.

Next, the surface of the one side of the metal wire 21, from which the masking parylene film is removed, is coated with the metal material 23, Teflon, epoxy or urethane, and then undergoes heat treatment (S2). In FIG. 5, only the anterior part of the metal wire 21 is coated with the white or ivory metal material 23, Teflon, epoxy or urethane, but not limited thereto. Alternatively, the remaining masking parylene film 27 as well as the anterior part may be coated with the metal material 23, Teflon, epoxy or urethane. Here, electroplating may be used for coating only the anterior part with the white metal material, and deposition may be used for coating even the masking parylene film 27 at the same time.

Then, the transparent parylene film 25 may be formed on only the white or ivory metal material 23, Teflon, epoxy or urethane or on both the white or ivory metal material 23, Teflon, epoxy or urethane and the masking parylene film 27, and undergoes the heat treatment (S3). In FIG. 5, the white or ivory metal material 23, Teflon, epoxy or urethane is coated on only the anterior part of the metal wire 21, so that the transparent parylene film 25 can be formed on both the white or ivory metal material 23, Teflon, epoxy or urethane coated on the anterior part and the masking parylene film 27 formed on the posterior part. Of course, in even this case, the transparent parylene film 25 can be formed on only the white or ivory metal material 23, Teflon, epoxy or urethane formed on the anterior part.

Next, the masking parylene film 27 and the transparent parylene film 25, or the masking parylene film 27, the white or ivory metal material 23, Teflon, epoxy or urethane, and the transparent parylene film 25, which are sequentially formed on the posterior part of the metal wire 21, are removed (S4). In other words, the masking parylene film remaining on the metal wire and the layers coated on the masking parylene film are removed.

FIG. 5 shows an example that the masking parylene film 27 and the transparent parylene film 25 are removed since the white or ivory metal material, Teflon, epoxy or urethane is not coated on the posterior part. Thus, the masking parylene film 27 or the like formed on the posterior part of the metal wire 21 can be removed by various methods. For example, the masking parylene film 27 or the like may be simply snicked and then taken off.

Below, each step of manufacturing the wire for straightening the irregular teeth according to an exemplary embodiment with the foregoing configuration will be described in detail. { 아래 문단 동일하여 생략 }

First, the metal wire 21 is manufactured with metal alloy. That is, the metal wire 21 is manufactured with one of nickel (Ni) alloy, stainless steel (SUS), NiTi, titaninum (Ti) alloy, copper (Cu) alloy, and aluminum (Al) alloy. Such a metal wire 21 has elastic and tensile force.

When the metal wire 21 is manufactured, the surface of the metal wire 21 is physically and chemically etched in accordance with the first and second exemplary embodiments. Further, the heat treatment is carried out. Before physically and chemically etching the surface of the metal wire 21, the surface of the metal wire 21 may be wet-cleaned by alkali, organic solvent, or ultra-pure water. That is, the surface of the metal wire 21 may be cleaned before physically and chemically etching it.

The surface of the metal wire 21 may be etched with an etching solution capable of forming a predetermined curve. In this exemplary embodiment, the etching solution produced by mixing one or mixture of $CuCl_2$, $FeCl_3$, HCl, $H_2SO_4$, $HNO_3$, $H_3PO_4$, HF and $H_2O_2$ with $H_2O$ or an organic solvent (e.g., methanol, ethanol, isopropylalcohol, etc.) may be used.

The metal wire 21 is electro- or electroless-etched to undergo surface treatment while being soaked into the etching solution. This surface treatment causes the surface of the metal wire 21 to have a predetermined curve. In other words, the metal wire 21 undergoes the surface treatment to have a curve with a width and depth of 0.1 μm to 50 μm. The surface-treated metal wire may be wet-cleaned by alkali, solvent, or water.

Figure 7:
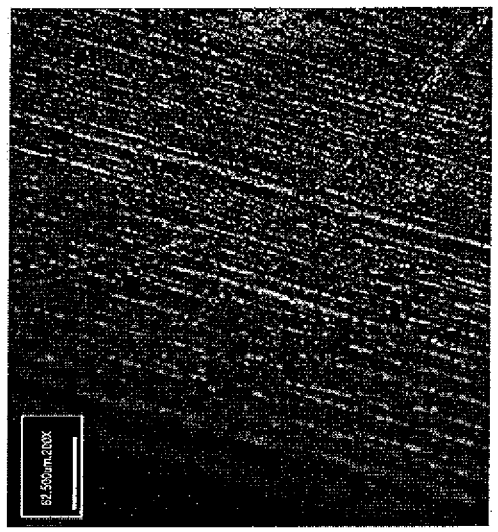
FIGS. 7 to 10 show microphotographs of the metal wire, the surface of which is treated, according to another exemplary embodiment of the present invention.
Figure 8:
Figure 9:
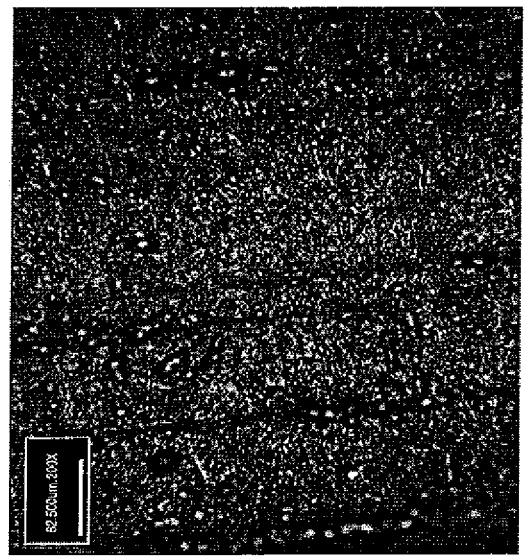
Figure 10:
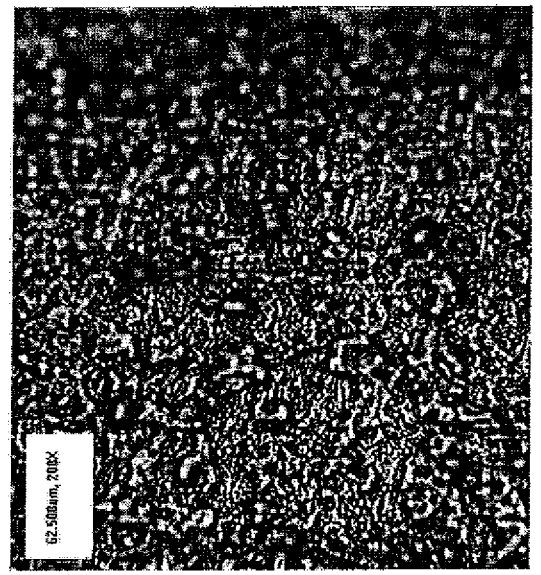

FIGS. 7 to 10 show microphotographs of the metal wire 21, the surface of which is electrochemically treated. FIG. 7 shows a microphotograph of the metal wire 21 of the stainless steel (SUS), which is etched by HCl for 20 minutes (at temperature of 45° C.). FIG. 8 shows a microphotograph of the metal wire 21 of the stainless steel (SUS), which is etched by a 1:2 sulfuric acid/water solution for 5 minutes (at temperature of 70° C.). FIG. 9 shows a microphotograph of the metal wire 21 of a NiTi material, which is etched by a $FeCl_3$ solution for 1 minute (at temperature of 40° C.). FIG. 10 shows a microphotograph of the metal wire 21 of a NiTi material, which is etched by a $FeCl_3$ solution for 1 minute (at temperature of 50° C.).

As above, the metal wire 21, physically or chemically etched to undergo the surface treatment, undergoes the heat treatment under a predetermined condition. The heat treatment performed after the chemical etching may be carried out in a vacuum chamber within atmospheric pressure or 0.1 mTorr, and proceeded for 1 minute to 48 hours at temperature of 50 to 600° C.

In accordance with the third and fourth exemplary embodiments, the process of masking the posterior part and the one side of the anterior part of the metal wire with the mask capable of covering the whole posterior part and the one side of the anterior part of the metal wire is performed before the surface treatment (physical or chemical etching) of the metal wire. Such a masking process is to prevent the parylene film from being formed on the posterior part and the one side of the anterior part of the metal wire.

As above, the mask may be an elastic tube, a box in which a masking part of the metal wire can be inserted, or a masking jig capable of preventing the masking part of the metal wire from being exposed to the outside. The mask may be made of polymer, metal or rubber. For example, the mask may be made of polymer such as silicon or the like, or rubber such as urethane or the like.

That is, the masking part of the wire for straightening the irregular teeth is configured with only the metal wire without the parylene film, so that the making part of the metal wire for straightening the teeth can apply strong force to the teeth and improve the sliding effect, thereby facilitating the straightening process for the teeth.

Thus, in accordance with the third and fourth exemplary embodiments, the masking part of the metal wire is masked with the mask for covering the masking part of the metal wire, then physically or chemically etched, and undergoes the heat treatment. The surface treatment and the heat treatment for the metal wire in accordance with the third and fourth exemplary embodiments are the same as those of the first and second exemplary embodiments. Also, the surface treatment and the heat treatment for the metal wire in accordance with the fifth exemplary embodiment are the same as above.

The surface of the metal wire 21 thermally treated under the foregoing condition is coated with the metal material 23, Teflon, epoxy or urethane to show white or ivory. The metal material deposited on the surface of the metal wire may be coated by wet electroplating or dry plating.

The metal material, Teflon, epoxy or urethane coated on the surface of the metal wire 21 may be formed by one of plasma sputtering, thermal vacuum evaporation, e-beam evaporation, ion plating, vacuum spraying, and wet electroplating.

The metal material deposited on the surface of the metal wire 21 and being white or ivory similar to the color of the teeth may be one or mixture of at least two among silver (Ag), zinc (Zn), tin (Sn), indium (In), platinum (Pt), tungsten (W), nickel (Ni), chrome (Cr), aluminum (Al), palladium (Pd), and gold (Au).

After coating the surface of the metal wire 21 with the white or ivory metal material, Teflon, epoxy or urethane, the surface of the metal wire 21 may be cleaned with ultrasonic waves using alkali, organic solvent, or ultra-pure water.

As above, the surface of the metal wire 21 is coated with the metal material 23, Teflon, epoxy or urethane having a thickness of 0.1 to 20 μm. After coating the surface of the metal wire 21 with the metal material 23, Teflon, epoxy or urethane, the heat treatment is performed.

The heat treatment performed after coating the surface of the metal wire 21 with the metal material, Teflon, epoxy or urethane may be performed in a vacuum chamber within atmospheric pressure or 0.1 mTorr, and proceeded for 1 minute to 48 hours at temperature of 50 to 600° C.

The white or ivory metal material, Teflon, epoxy or urethane thermally treated as above undergoes the surface treatment. In other words, the white or ivory metal material, Teflon, epoxy or urethane thermally treated as above is chemically etched. Then, the heat treatment is performed. Such a process is need for allowing the transparent parylene film or the transparent oxide film to be easily formed on the white or ivory metal material, Teflon, epoxy or urethane.

However, the surface treatment for the white or ivory metal material, Teflon, epoxy or urethane is not indispensable but optional.

In the case where the surface of the metal material 23, Teflon, epoxy or urethane is chemically etched, a predetermined etching solution is used. That is, the surface of the metal material 23, Teflon, epoxy or urethane is etched by an etching solution produced by mixing one or mixture of HCl, $H_2SO_4$, $HNO_3$, $H_2O_2$ with $H_2O$.

Figure 11:
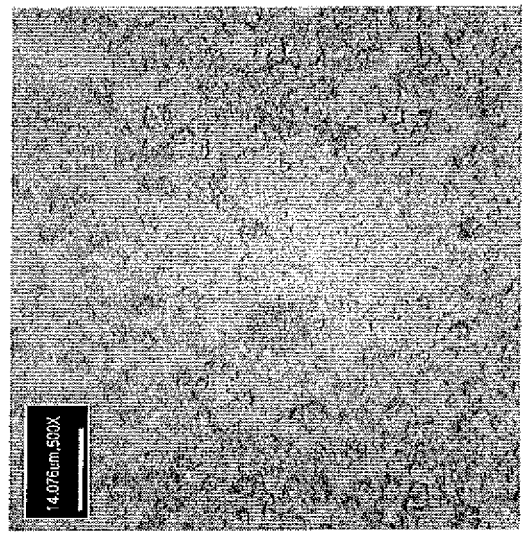
FIGS. 11 and 12 show microphotographs of the metal wire, the surface of which is treated with a white metal material, according to another exemplary embodiment of the present invention.
Figure 12:
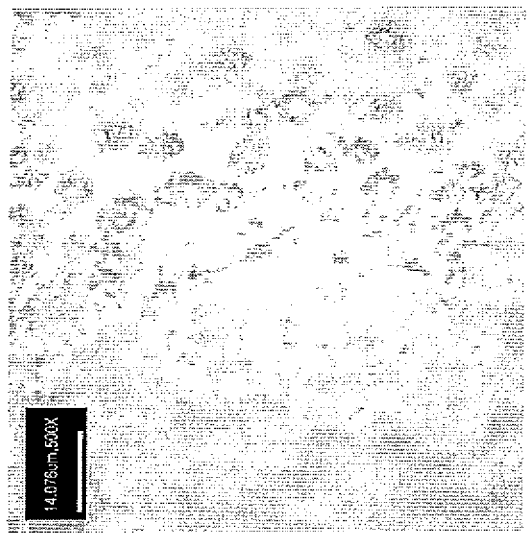

FIG. 11 is a microphotograph (500 magnification) showing that the surface of the NiTi metal wire is coated with the metal material 23 and then the surface of the metal material 23 is etched using a mixed solution of $HNO_3$ and $H_2O$ for 18 seconds, and FIG. 12 is a microphotograph (500 magnification) showing that the surface of the SUS metal wire is coated with the metal material 23 and then the surface of the metal material 23 is etched using a mixed solution of $HNO_3$ and $H_2O$ for 50 seconds.

Using the foregoing etching solution, the surface of the metal material 23 is etched for 1 second to 5 minutes at temperature of 10° C. to 100° C. After the surface of the metal material 23 or the like is chemically etched, the heat treatment is carried out. The heat treatment performed after chemically etching the surface of the metal material or the like is carried out in a vacuum chamber within atmospheric pressure or 0.1 mTorr, and proceeded for 1 minute to 48 hours at temperature of 50° C. to 600° C.

After the metal material 23 or the like undergoes the surface etching and the heat treatment, the transparent metal oxide layer 24 is coated and then the transparent parylene film is formed (refer to the second and fourth exemplary embodiment), or the transparent parylene film is directly formed without coating the transparent metal oxide film 24 (refer to the first and third exemplary embodiment).

The transparent metal oxide film 24 is formed on the metal material 23 by one of sputtering, thermal vacuum evaporation, e-beam evaporation, and ion plating.

Meanwhile, the transparent metal oxide film 24 may be formed on the meal material 23 by coating a raw material of nano-sized particles in a sol state through a vacuum spraying method.

The transparent metal oxide film 24 may be formed by various metal oxides as long as it can be transparent. In this exemplary embodiment, the transparent metal oxide film 24 may be one or mixture of at least two among ITO, ZnO, $TiO_2$, $Al_2O_3$, $Ta_2O_5$, $ZrO_2$, $SiO_2$, $GeO_2$, $Y_2O_3$, $La_2O_3$, $HfO_2$, CaO, $In_2O_3$, $SnO_2$, MgO, $WO_2$, and $WO_3$.

The transparent metal oxide film 24 formed as above has to be formed to have a wearable thickness when the wire for straightening the irregular teeth is mounted to the teeth. Approximately, the transparent metal oxide film 24 may be coated to have a thickness of 1 nm to 1 μm.

When the transparent metal oxide film 24 is deposited in a vacuum, it may be carried out at temperature of 15° C. to 300° C. in the vacuum chamber. Here, the transparent metal oxide film 24 is formed by injecting oxygen gas of 1 to 200 sccm into the vacuum chamber. Further, the transparent meal oxide film 24 is formed by a plasma process, in which argon gas of 50 sccm to 500 sccm is injected and a chamber pressure of 1 to 20 mTorr is maintained during the plasma process of the transparent metal oxide film.

As above, after the transparent metal oxide film 24 is formed on the metal material 23, the transparent parylene film 25 is formed on the transparent metal oxide film 24 and undergoes the heat treatment. Thus, the parylene film 25 is coated to prevent the white or ivory metal material 23, Teflon, epoxy or urethane from discoloration and to form the wire for straightening the irregular teeth, which is harmless to a human body. The transparent parylene film may have a thickness of 1 μm to 50 μm in consideration of a wearing sensation.

In the meantime, the first to third exemplary embodiments of the present invention do not involve the process of forming the foregoing transparent metal oxide film 24. In other words, the transparent parylene film is directly formed on the white metal material.

After forming the transparent parylene film, the heat treatment is performed, and in accordance with first and second exemplary embodiments, one side of the foregoing coating layer formed on the metal wire is removed and undergoes the surface treatment to be made smooth. The one side of the metal wire, from which the coating layer is removed, is a part to contact the teeth.

The transparent parylene film 25 is formed using a dimer on the transparent metal oxide film 24. Here, the transparent parylene film 25 is formed using at least one of C(Di-chloro-para-xylylene)-type (refer to (a) of FIG. 6), N(Di-para-xylylene)-type (refer to (b) of FIG. 6), D(Tetra-chloro-para-xylylene)-type (refer to (c) of FIG. 6), F(Octafluoro-[2,2] para-xylylene)-type (refer to (d) of FIG. 6), HT-type (refer to (e) of FIG. 6), A-type (refer to (f) of FIG. 6), and AM-type (refer to (g) of FIG. 6) dimers.

The transparent parylene film 25 is formed by vaporizing the dimer in a vaporizer at temperature of 50 to 250° C., dissociating the dimer into a monomer while passing through a pyrolysis at temperature of 550 to 850° C., and depositing the monomers on the surface of the transparent metal oxide film while maintaining a partial pressure of the monomer at 10 to 100 mTorr in the vacuum chamber.

After forming the transparent parylene film 25 as above, the heat treatment is performed. The heat treatment is carried out in a vacuum chamber within atmospheric pressure or 0.1 mTorr, and proceeded for 1 minute to 48 hours at temperature of 50° C. to 250° C. Through the heat treatment, coherence between the elements of the wire for straightening the irregular teeth is improved, thereby enhancing the whole strength.

Although the present invention has been described with reference to the embodiments and the accompanying drawings, the present invention is not limited to these embodiments and the drawings. It should be understood that various modifications, additions and substitutions can be made by a person having ordinary knowledge in the art without departing from the scope and spirit of the invention as disclosed in the accompanying claims.

INDUSTRIAL APPLICABILITY

According to exemplary embodiments of the present invention, there is provided a method of manufacturing a wire for straightening irregular teeth, which can be applied to manufacturing industry for the wire for straightening the irregular teeth, and industry of the wire used in a dental clinic for straightening the irregular teeth.

The invention claimed is:

1. A method of manufacturing a wire for straightening irregular teeth, the method comprising
manufacturing a metal wire with metal alloy;
physically or chemically etching a surface of the metal wire and then performing heat treatment;
coating the surface of the metal wire with a metal material to show white or ivory and then performing heat treatment;
forming a transparent parylene film on the metal material and then performing heat treatment;
removing an entirety of one side of the foregoing coating layer of the metal material and transparent parylene film from the surface of the metal wire; and
applying surface treatment to the entirety of one side with the coating layer of the metal material and transparent parylene film removed.

2. The method according to claim 1, wherein the metal wire comprises one of stainless steel, NiTi, nickel (Ni) alloy, titanium (Ti) alloy, copper (Cu) alloy, and aluminum (Al) alloy.

3. The method according to claim 1, wherein the metal material coated on the surface of the metal wire comprises one or mixture among silver (Ag), zinc (Zn), tin (Sn), indium (In), platinum (Pt), tungsten (W), nickel (Ni), chrome (Cr), aluminum (Al), palladium (Pd), and gold (Au).

4. The method according to claim 1, wherein the surface of the metal wire is coated with the white or ivory metal material, and then cleaned with ultrasonic waves using alkali, organic solvent, or ultra-pure water.

5. The method according to claim 1, wherein the transparent parylene film comprises at least one of C(Di-chloro-para-xylylene)-type, N(Di-para-xylylene)-type, D(Tetra-chloro-para-xylylene)-type, F(Octafluoro-[2,2]para-xylylene)-type, HT-type, A-type, and AM-type dimers.

6. A method of manufacturing a wire for straightening irregular teeth, the method comprising
manufacturing a metal wire with metal alloy;
physically or chemically etching a surface of the metal wire and then performing heat treatment;
coating the surface of the metal wire with a metal material to show white or ivory and then performing heat treatment;
coating a transparent metal oxide film on the metal material coated on the surface of the metal wire;
forming a transparent parylene film on the transparent metal oxide film and then performing heat treatment;
removing an entirety of one side of the foregoing coating layer of the metal material and parylene film from the surface of the metal wire; and
applying surface treatment to the entirety of one side with the coating layer of the metal material and transparent parylene film removed.

7. The method according to claim 6, wherein the metal wire comprises one of stainless steel, NiTi, nickel (Ni) alloy, titanium (Ti) alloy, copper (Cu) alloy, and aluminum (Al) alloy.

8. The method according to claim 6, wherein the metal material coated on the surface of the metal wire comprises one or mixture among silver (Ag), zinc (Zn), tin (Sn), indium (In), platinum (Pt), tungsten (W), nickel (Ni), chrome (Cr), aluminum (Al), palladium (Pd), and gold (Au).

9. The method according to claim 6, wherein the surface of the metal wire is coated with the white or ivory metal material, and then cleaned with ultrasonic waves using alkali, organic solvent, or ultra-pure water.

10. The method according to claim 6, wherein the transparent metal oxide film comprises one or mixture of ITO, ZnO, $TiO_2$, $Al_2O_3$, $Ta_2O_5$, $ZrO_2$, $SiO_2$, $GeO_2$, $Y_2O_3$, $La_2O_3$, $HfO_2$, CaO, $In_2O_3$, $SnO_2$, MgO, $WO_2$, and $WO_3$.

11. The method according to claim 6, wherein the transparent parylene film comprises at least one of C(Di-chloro-para-xylylene)-type, N(Di-para-xylylene)-type, D(Tetra-chloro-para-xylylene)-type, F(Octafluoro-[2,2]para-xylylene)-type, HT-type, A-type, and AM-type dimers.

12. A method of manufacturing a wire for straightening irregular teeth, the method comprising
manufacturing a metal wire with metal alloy;
forming a masking parylene film on a surface of the metal wire and then removing the masking parylene film from one side of the metal wire or one side of an anterior part;
physically or chemically etching a surface of the one side of the metal wire with the masking parylene film removed and then performing heat treatment;
coating a metal material, Teflon, epoxy or urethane of the surface of the one side of the metal wire, from which the masking parylene film is removed, to show white or ivory and then performing heat treatment;
forming a transparent parylene film on the metal material, Teflon, epoxy or urethane and then performing heat treatment; and
removing the masking parylene film remaining on the metal wire and the coating layer on the masking parylene film.

13. The method according to claim 12, wherein the metal wire comprises one of stainless steel, NiTi, nickel (Ni) alloy, titanium (Ti) alloy, copper (Cu) alloy, and aluminum (AD alloy.

14. The method according to claim 12, wherein the metal material coated on the surface of the metal wire comprises one or mixture among silver (Ag), zinc (Zn), tin (Sn), indium (In), platinum (Pt), tungsten (W), nickel (Ni), chrome (Cr), aluminum (Al), palladium (Pd), and gold (Au).

15. The method according to claim 12, wherein the surface of the metal wire is coated with the white or ivory metal material, Teflon, epoxy or urethane, and then cleaned with ultrasonic waves using alkali, organic solvent, or ultra-pure water.

16. The method according to claim 12, wherein the transparent parylene film comprises at least one of C(Di-chloro-para-xylylene)-type, N(Di-para-xylylene)-type, D(Tetra-chloro-para-xylylene)-type, F(Octafluoro-[2,2]para-xylylene)-type, HT-type, A-type, and AM-type dimers.

* * * * *

UNITED STATES PATENT AND TRADEMARK OFFICE
CERTIFICATE OF CORRECTION

| | | |
|---|---|---|
| PATENT NO. | : 8,778,444 B2 | Page 1 of 1 |
| APPLICATION NO. | : 13/130122 | |
| DATED | : July 15, 2014 | |
| INVENTOR(S) | : In Jae Kim | |

It is certified that error appears in the above-identified patent and that said Letters Patent is hereby corrected as shown below:

In the Claims

Claim 13 (column 14, line 48)

"...titanium (Ti) alloy, copper (Cu) alloy, and aluminum (AD..." should read --...titanium (TI) alloy, copper (Cu) alloy, and aluminum (Al)...--

Signed and Sealed this
Twenty-eighth Day of October, 2014

Michelle K. Lee
*Deputy Director of the United States Patent and Trademark Office*